United States Patent
Doshi et al.

(10) Patent No.: US 6,761,687 B1
(45) Date of Patent: Jul. 13, 2004

(54) SPECULUM

(76) Inventors: Umesh C. P. Doshi, 36/38 Haig Road, Singapore (SG), 438740; Wah Ling Joel Lee, c/o Singapore Polytechnic 500 Dover Road, Singapore (SG), 139651

(*) Notice: Subject to any disclaimer, the term of this patent is extended or adjusted under 35 U.S.C. 154(b) by 406 days.

(21) Appl. No.: 09/913,497

(22) PCT Filed: Nov. 2, 2000

(86) PCT No.: PCT/SG00/00181

§ 371 (c)(1), (2), (4) Date: Jun. 21, 2002

(87) PCT Pub. No.: WO01/43627

PCT Pub. Date: Jun. 21, 2001

(30) Foreign Application Priority Data

Dec. 17, 1999 (GB) .............................................. 9929826

(51) Int. Cl.[7] ................................................ A61B 1/00
(52) U.S. Cl. ........................ 600/184; 600/210; 600/219
(58) Field of Search ................................ 600/184, 190, 600/193, 196, 197, 199, 208, 210, 212, 213, 215, 220, 219, 222, 223, 245

(56) References Cited

U.S. PATENT DOCUMENTS

| | | | | |
|---|---|---|---|---|
| 3,774,596 A | * | 11/1973 | Cook ........................ | 600/184 |
| 4,380,998 A | * | 4/1983 | Kieffer et al. .............. | 600/200 |
| 4,807,593 A | * | 2/1989 | Ito .............................. | 600/114 |
| 5,135,526 A | | 8/1992 | Zinnanti et al. | |
| 5,293,862 A | * | 3/1994 | O'Hara et al. .............. | 600/186 |
| 5,392,764 A | | 2/1995 | Swanson et al. | |
| 5,716,329 A | | 2/1998 | Dieter | |
| 6,142,931 A | * | 11/2000 | Kaji ........................... | 600/114 |
| 6,450,977 B1 | * | 9/2002 | Baxter-Jones ............... | 600/591 |
| 6,497,654 B1 | * | 12/2002 | Leonard et al. ............. | 600/245 |

FOREIGN PATENT DOCUMENTS

| | | |
|---|---|---|
| GB | 2090531 A | 11/1981 |
| GB | 2 090 531 A | 7/1982 |
| GB | 2275421 A | 2/1993 |
| GB | 2 275 421 A | 8/1994 |
| WO | WO 93/07800 | 3/1993 |
| WO | WO 93/07800 A1 | 4/1993 |
| WO | WO 97/24975 | 7/1997 |
| WO | WO 97/24975 A1 | 7/1997 |

OTHER PUBLICATIONS

PCT International Search Report dated Jan. 11, 2001.

* cited by examiner

*Primary Examiner*—Beverly M. Flanagan

(57) ABSTRACT

A speculum according to the invention comprises two parts, an outer member (1) and an inner member (2). The outer member (1) comprises a tubular body (3) having an anterior end (4) with an opening (6) and a posterior end (5) with an opening (7). An elongate slot (11) is formed in the side wall (12) of the tubular body (3), extending from the opening (7) at the posterior end (5) towards the anterior end (4). The inner member (2) of the speculum comprises a cup-shaped body (13) having an anterior end (14) formed as a plug (16) and a posterior end (15) with an opening (17). An elongate key member (18) is formed in the side wall (19) of the cup-shaped body (13), extending from the opening (17) at the posterior end (15) towards the anterior end (14). The speculum is assembled by inserting the inner member (2) within the outer member (3) and aligning the key member (18) with the elongate slot (11). When the spectrum has been inserted within a body cavity, the inner member (2) may be removed and the outer member (3) may be rotated to align the elongate slot (11) with a site of interest in the cavity wall, thus allowing a user to examine tissue in the body cavity or to have access to sites of required surgical procedures.

22 Claims, 1 Drawing Sheet

SPECULUM

Figure 1A:
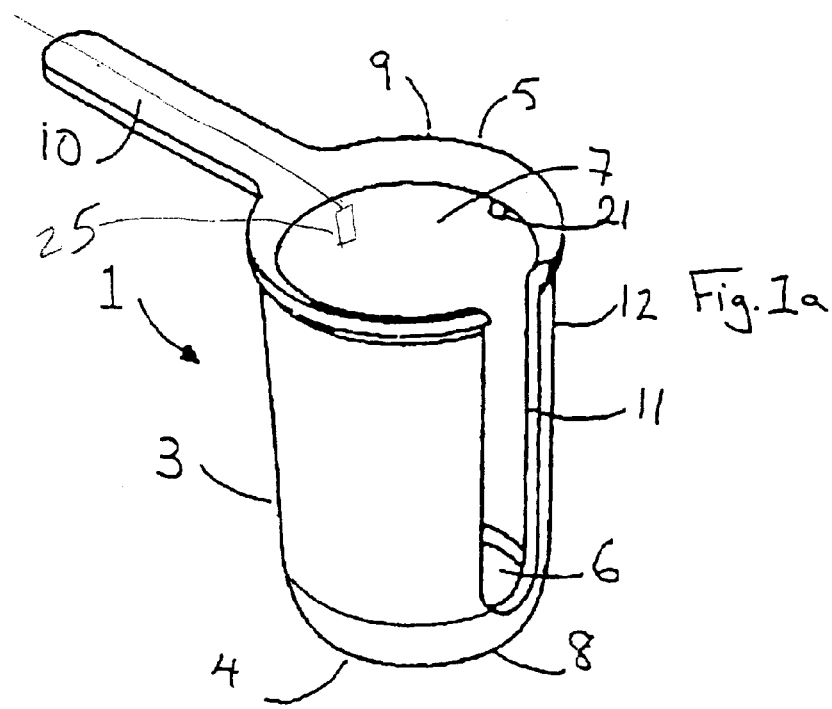

The invention relates to a speculum, particularly, though not exclusively to a gynaecological speculum for assisting in the identification and repair of vaginal and cervical lacerations.

A speculum is used in a variety of medical procedures to dilate an orifice to a cavity in order to examine or operate within the cavity. A number of different types of gynaecological speculum are used to dilate the vaginal orifice to allow access to the vaginal cavity for medical examinations or surgical procedures. The most commonly used type is known as a duck-billed speculum which has two portions that are inserted into the vaginal cavity and separated from one another by the action of closing a handle portion. This type of speculum is often uncomfortable for the patient and also allows tissue to protrude into the gap between the duck-bills and to be exposed on each side of the duck-bills. Various types of speculum have been proposed that comprise a tubular section for insertion into the vaginal cavity. These types of speculum have an open insertion end for insertion into the vaginal cavity and an open user end allowing access into the vaginal cavity through the speculum during medical examinations or surgical procedures.

A particular requirement for a vaginal speculum is to allow access to the vagina for repair of tears in the vaginal wall following the birth of a baby. Occasionally after a normal delivery of a baby and often after an assisted delivery using, for example, forceps or vacuum extraction, there are tears or lacerations along the lateral walls of the vagina. These tears can become quite difficult to detect after a delivery as the tissue in the vagina is oedematous and haemorrhagic. As well as bleeding from the tears themselves, there is usually bleeding from the contracting uterus. All this makes it difficult for the tears in the wall to be seen and repaired if necessary.

It is an object of the present invention to provide a speculum, and in particular a speculum suitable for use as a vaginal speculum, that provides improved visibility and access for repair of torn tissue or other surgical procedures.

The invention provides a speculum comprising:

an outer member comprising a tubular body having an anterior end, a posterior end and a side wall, the anterior end having an opening and the posterior end having an opening and the side wall of the tubular body comprising a slot opening extending along a portion of the side wall of the tubular body; and an inner member comprising a cup-shaped body having an anterior end and a posterior end and a side wall, the cup-shaped body being insertable within the tubular body of the outer member, the anterior end being closed and the posterior end having an opening.

Preferably the slot in the outer member tubular body extends from the posterior opening along the side wall in the direction of the interior opening.

Preferably the inner member cup-shaped body comprises a key member extending along side wall of the cup-shaped body and corresponding to the slot opening in the side wall of the tubular body.

Preferably the key member in the inner member cup-shaped body extends from the posterior opening along the side wall in the direction of the closed anterior end. Preferably the key member comprises a protrusion on the outer surface of the side wall of the cup-shaped body.

Preferably means are provided to rotate the outer member tubular body within a cavity within which it may be inserted such that the slot in the side wall may be aligned with any site of a required examination or surgical procedure in the wall of the cavity.

Preferably the outer member further comprises handle means at the posterior end. The handle means provides improved ease of insertion by a user and allows the speculum to be rotated within the cavity when inserted.

The cup-shaped body of the inner member is inserted into the interior of the tubular body of the outer member. Advantageously the cup-shaped body is sized to form a close fit within the tubular body. Preferably the closed anterior end of the cup-shaped body forms a seal within the opening in the anterior end of the tubular body. Advantageously the closed anterior end of the cup-shaped body is shaped with a ridge to co-operate with the rim of the opening in the anterior end of the tubular body. Alternatively a sealing ring or gasket may be provided.

In use, the cup-shaped body of the inner member is inserted into the tubular member. The assembled cup shaped body and tubular body are inserted into an orifice such that the outer tubular body dilates the orifice in which it is inserted and maintains the tissue within the cavity around the outer surface of the tubular body. The key member in the side wall of the cup-shaped body is positioned in correspondence with the slot in the tubular body. Once the speculum is in position within the cavity, the inner cup-shaped body is removed. The tubular body can be rotated within the cavity to align the slot in the tubular body with any site of a required examination or surgical procedure in the cavity wall either in combination with the cup-shaped body inserted therein or when the cup-shaped body has been removed.

Advantageously resilient retention means are provided to retain the cup-shaped body within the tubular body. Preferably the cup-shaped body is provided with resilient retention means to retain the cup-shaped body within the tubular body. Advantageously the resilient retention means comprise resilient latch means and the tubular body further comprises co-operating retention means. Advantageously the latch means and the retention means also serve as alignment means to align the key member in the side wall of the cup-shaped body with the slot in the side wall of the tubular body when the cup-shaped body is inserted therein.

Preferably the edges of the anterior and posterior openings on the tubular body are smooth to assist with insertion and removal of the speculum into and from the cavity and to minimise discomfort to the patient. Advantageously the tubular body is provided with a lip to assist in position the tubular body within the cavity and to provide resistance against the tubular body slipping out of the cavity in use.

Advantageously the outer member and/or the inner member are formed from injection moulded plastics material.

Preferably the outer member and/or the inner member are formed from transparent materials.

Advantageously the speculum further comprises a light source to aid and/or enhance the visual examination of sites of interest within the body orifice (FIG. 1a). Preferably the light source comprises a fibre-optic or LED type light source. Advantageously the light source 25 is positioned within the side the wall 12 of the outer member 1. If the light source 25 is a fibre optic, it is preferably fed through the handle 10 of the outer member 1 and extends within the side wall 12 of the tubular body 3. If the light source 25 is an LED, it is preferably positioned within the side wall 12 of the tubular body 3 and is connected to a power source via a connection fed through the handle 10 of the outer member 1.

The invention further provides a method of inserting a spectrum within a body cavity comprising steps of:

assembling an inner member comprising a cup-shaped body within an outer member comprising a tubular body, the tubular body having an anterior end, a posterior end and a side wall, the anterior end having an opening, the posterior end having an opening and the side wall of the outer member tubular body comprising a slot opening extending along a portion of the side wall of the tubular body, the cup-shaped body having an anterior end, a posterior end and a side wall;

inserting the assembled inner and outer members within a body cavity;

removing the inner member from the outer member; and positioning the slot opening in the outer member with respect to a site in a wall of the cavity.

Preferably the side wall if the inner member cup-shaped body comprises a key member extending along a portion of the side wall of the cup-shaped body and corresponding to the slot opening in the side wall of the tubular body and the step of assembling the inner member within the outer member includes the step of aligning the key member in the cup-shaped body with the slot opening in the tubular body.

Preferably the tubular body is rotated to align the slot with any site of a required examination or surgical procedure once the cup-shaped body has been removed from the tubular body. Alternatively, if the tubular body and cup-shaped body are made from transparent materials, the assembled cup-shaped and tubular bodies may be rotated together to align the slot in the side wall of the tubular body with a site in the cavity wall.

Preferably the interior of the tubular body is illuminated by a light source such as a fibre optic or LED source to aid and enhance the visual examination of the site in the cavity wall.

Figure 1B:
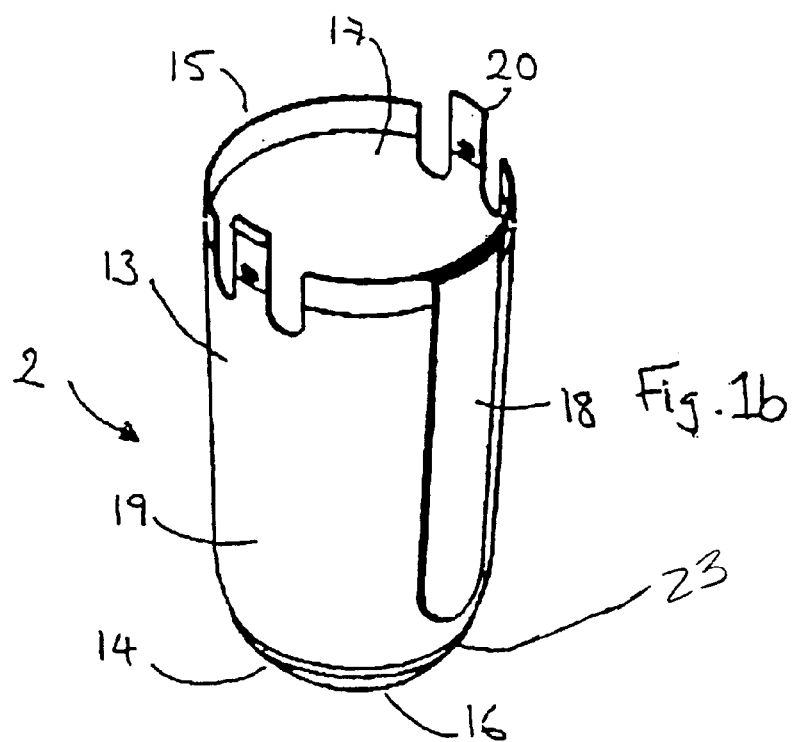

The invention will now be described, by way of example, only, by reference to the accompanying drawings, of which:

FIG. 1a shows a perspective view of an outer member of a speculum according to the invention; and FIG. 1b shows a perspective view of an inner member of a speculum according to the invention.

A speculum according to the invention comprises two parts, an outer member 1 shown in FIG. 1a and an inner member 2 as shown in FIG. 1b.

The outer member 1 comprises a tubular body 3 having an anterior end 4 and a posterior end 5. The tubular body 3 has an opening 6 at the anterior end 4 and an opening 7 at the posterior end 5. The rim 8 of the opening 6 is formed with a smooth edge to minimise discomfort for a patient as the outer member is inserted within a body cavity, such as a vaginal cavity, when in use. The opening 7 at the posterior end 5 allows a doctor or other user to have visual and physical access to the interior of the speculum to carry out medical examinations and/or surgical procedures as necessary.

The opening 7 is formed with a lip 9 to assist in retaining the speculum within a body cavity in use. A handle 10 is integrally formed with the lip 9 to provide a means for a user to hold the speculum during insertion and removal from a body cavity and to allow rotation of the speculum within the body cavity in use.

An elongate slot 11 is formed in the side wall 12 of the tubular body 3, extending from the opening 7 at the posterior end 5 towards the anterior end 4. The elongate slot 11 allows a user access to the side walls of the body cavity in which the speculum is inserted in use.

The inner member 2 is inserted within the outer member 1 and the combined assembly is inserted within a body cavity. The inner member 2 comprises a cup-shaped body 13 having an anterior end 14 and a posterior end 15. The anterior end 14 is formed as a plug to close the end of the cup-shaped body 13. The posterior end 15 has an opening 17 which allows a doctor or other user to have visual and physical access to the interior of the speculum.

An elongate key member 18 is formed in the side wall 19 of the cup-shaped body 13, extending from the opening 17 at the posterior end 15 towards the anterior end 14. The elongate key member 18 is aligned with the elongate slot 11 in the outer member 1 and thus holds the inner member 2 in position with respect to the outer member 1.

The inner member 2 is formed as a close fit within the tubular body 3 of the outer member 1. When the cup-shaped body 13 of the inner member 2 is inserted within the tubular body 3 of the outer member 1, the plug 16 at the anterior end 14 of the cup-shaped body 13 fits into the opening 6 at the anterior end 4 of the tubular body 3. A groove 23 around the plug 16 co-operates with the rim 8 of the opening 6 to form a seal.

Resilient latch means 20 are formed integrally with the side wall 19 of the cup-shaped body 13 for co-operation with retention means 21 integrally formed in the side wall 12 of the tubular body 3. When the cup-shaped body 13 is inserted within the tubular body 3 the latch means 20 engage with the retention means 21 to hold the cup-shaped body 13 within the tubular body 3. The cup-shaped body 13 can be removed from the tubular body 3 by deformation of the latch means 20 to disengage them from the retention means 21. The engagement of the latch means 20 with the retention means 21 can also serve to align the key member 18 in the cup-shaped body 13 with the slot 11 in the tubular body 3.

In use therefore, the cup-shaped body 13 of the inner member 2 is inserted into the tubular body 3 of the outer member 1. The combined inner and outer members 2,3 are then inserted within a body cavity (not shown) such as a vaginal cavity. The side wall 12 of the tubular body 3 holds the tissue of the body cavity in an extended position and the plug 16 at the end of the cup-shaped body 13 forms a seal with the rim 8 around the hole 6 at the end 4 of the tubular body 3. This has the advantage that it also prevents ingress of fluids or other matter into the interior of the speculum as the speculum is inserted into the body cavity. The key member 18 in the side wall 19 of the cup-shaped body 13 is aligned with the slot 11 in the side wall 12 of the tubular body 3 and the combined inner and outer members 1,2 can be rotated within the body cavity, by means of the handle 10. The inner member 2 is then removed from the outer member 1 and the tubular body 3 is rotated by means of the handle 10 until the slot 11 is positioned over a laceration in the wall of the body cavity. The user, such as a doctor, may then repair the laceration without the repair site being obscured by blood, for example.

The speculum of the invention thus has the advantage that oedematous vaginal mucosa or the tissue of other cavities can be pushed away and fluids and other matter are prevented from entering the interior of the speculum as the speculum is positioned within a body cavity. The outer member of the speculum may be rotated within the body cavity to a site of interest, thus enabling a user to examine the tissue of the wall of a cavity and to identify easily the apex of a laceration or the site of a required surgical procedure. The inclusion of a light source within the speculum also improves the visual access to the cavity.

What is claimed is:

1. A speculum comprising:

an outer member comprising a tubular body having an anterior end, a posterior end and a side wall, the anterior end having an opening and the posterior end having an opening and the side wall of the tubular body comprising a slot opening extending along a portion of the side wall of the tubular body; and an inner member comprising a cup-shaped body having an anterior end and a posterior end and a side wall, the cup-shaped body being insertable within the tubular body of the outer member, the anterior end being closed and the posterior end having an opening, wherein the inner member cup-shaped body comprises a key member extending along the side wall of the cup-shaped body and corresponding to the slot opening in the side wall of the tubular body.

2. A speculum according to claim 3 wherein the slot in the outer member tubular body extends from the posterior opening along the side wall in the direction of the anterior opening.

3. A speculum according to claim 1 wherein the key member in the inner member cup-shaped body extends from the posterior opening along the side wall in the direction of the closed anterior end.

4. A speculum according to claim 1 wherein the key member comprises a protrusion on the outer surface of the side wall of the cup-shaped body.

5. A speculum according to claim 1 wherein means are provided to rotate the outer member tubular body within a cavity within which it may be inserted.

6. A speculum according to claim 5 wherein the means to rotate the outer member tubular body comprises handle means at the posterior end of the tubular body.

7. A speculum according to claim 1 wherein the cup-shaped body is sized to form a close fit within the tubular body.

8. A speculum according to claim 1 wherein the closed anterior end of the cup-shaped body forms a seal within the opening in the anterior end of the tubular body.

9. A speculum according to claim 8 wherein the closed anterior end of the cup-shaped body is shaped with a ridge to co-operate with a rim of the opening in the anterior end of the tubular body.

10. A speculum according to claim 8 wherein a seal is provided between a ring of the outer member and a groove of the inner member.

11. A speculum according to claim 1 wherein resilient retention means are provided to retain the cup-shaped body within the tubular body.

12. A speculum according to claim 1 wherein resilient retention means are provided to retain the cup-shaped body within the tubular body and wherein the retention means also serve as alignment means to align the key member in the side wall of the cup-shaped body with the slot in the side wall of the tubular body when the cup-shaped body is inserted therein.

13. A speculum according to claim 11 wherein the resilient retention means comprise resilient latch means on the cup-shaped body and co-operating retention means on the tubular body.

14. A speculum according to claim 1 wherein the tubular body is provided with a lip.

15. A speculum according to claim 1 wherein the outer member and/or the inner member are formed from injection moulded plastics material.

16. A speculum according to claim 1 wherein the outer member and/or the inner member are formed from transparent materials.

17. A speculum according to claim 1 wherein the speculum further comprises a light source to aid and/or enhance the visual examination of sites of interest within the body orifice.

18. A speculum according to claim 17 wherein the light source comprises a fibre-optic or LED light source.

19. A speculum according to claim 17 wherein the light source (25) is positioned within the side wall (12) of the outer member (1).

20. A method of inserting a speculum within a body cavity comprising steps of:

assembling an inner member comprising a cup-shaped body within an outer member comprising a tubular body, the tubular body having an anterior end, a posterior end and a side wall, the anterior end having an opening, the posterior end having an opening and the side wall of the outer member tubular body comprising a slot opening extending along a portion of the side wall of the tubular body, the cup-shaped body having an anterior end, a posterior end and a side wall;

inserting the assembled inner and outer members within a body cavity;

removing the inner member from the outer member; and positioning the slot opening in the outer member with respect to a site in a wall of the cavity, wherein the side wall of the cup-shaped body comprises a key member extending along a portion of the side wall of the cup-shaped body and corresponding to the slot opening in the side wall of the tubular body and the step of assembling the inner member within the outer member includes the step of aligning the key member in the cup-shaped body with the slot opening in the tubular body.

21. A method according to claim 20 wherein the tubular body is rotated to align the slot with any site of a required examination or surgical procedure once the cup-shaped body has been removed from the tubular body.

22. A method according to claim 20 wherein the interior of the tubular body is illuminated by a light source such as a fibre optic or LED source to aid and enhance the visual examination of the site in the cavity wall.

* * * * *